United States Patent
Gunsel et al.

(10) Patent No.: US 6,667,284 B2
(45) Date of Patent: Dec. 23, 2003

(54) LUBRICANT FOR MAGNETIC RECORDING MEDIUM AND USE THEREOF

(75) Inventors: Selda Gunsel, The Woodlands, TX (US); Clifford Venier, The Woodlands, TX (US); I-Ching Chiu, Houston, TX (US)

(73) Assignee: Pennzoil-Quaker State Company, Houston, TX (US)

( * ) Notice: Subject to any disclaimer, the term of this patent is extended or adjusted under 35 U.S.C. 154(b) by 18 days.

(21) Appl. No.: 09/814,887

(22) Filed: Mar. 22, 2001

(65) Prior Publication Data

US 2003/0108777 A1 Jun. 12, 2003

Related U.S. Application Data

(60) Provisional application No. 60/126,372, filed on Mar. 26, 1999.

(51) Int. Cl.$^7$ ............... C10M 137/10; C10M 135/00; C10M 133/16; C10M 133/54; C10M 129/16
(52) U.S. Cl. ............. 508/463; 508/433; 508/459; 508/595; 508/551; 508/579; 508/583; 558/208; 558/209; 562/503; 564/80; 564/189; 568/838
(58) Field of Search ............. 508/433, 463, 508/459, 548, 545, 551, 579, 583; 558/208, 209; 562/503; 564/80, 189; 568/838

(56) References Cited

U.S. PATENT DOCUMENTS

| | | | |
|---|---|---|---|
| 2,912,447 A | * 11/1959 | Brannock | ............... 554/229 |
| 3,855,105 A | * 12/1974 | Diveley | ............... 508/463 |
| 4,566,983 A | 1/1986 | Hayashi | |
| 4,693,799 A | 9/1987 | Yanagihara et al. | |
| 4,721,823 A | 1/1988 | Venier et al. | |
| 4,849,566 A | 7/1989 | Venier et al. | |
| 4,929,782 A | 5/1990 | Venier et al. | |
| 5,012,022 A | 4/1991 | Venier et al. | |
| 5,012,023 A | 4/1991 | Venier et al. | |
| 5,026,577 A | 6/1991 | Biresaw et al. | |
| 5,084,516 A | 1/1992 | Tsuchiya et al. | |
| 5,093,016 A | * 3/1992 | Colombo | ............... 508/463 |

(List continued on next page.)

FOREIGN PATENT DOCUMENTS

| | | |
|---|---|---|
| EP | 0613886 A1 | 9/1994 |
| EP | 0613887 A1 | 9/1994 |
| JP | 58222441 A | 12/1983 |
| JP | 10140169 | 5/1998 |
| WO | WO 98/07145 | 2/1998 |

OTHER PUBLICATIONS

Tetramethylolcyclopentanol esters as lubricating base oils' by Man\med'yarov, M.A. et al ; Khimiya i Tekhonologiya Topliv i Masel ; 1991, (6) 26–28.*

(List continued on next page.)

*Primary Examiner*—Jacqueline V. Howard
(74) *Attorney, Agent, or Firm*—Jenkens & Gilchrist

(57) ABSTRACT

A magnetic recording medium and method for forming the magnetic recording medium are described. The magnetic recording medium includes a magnetic layer formed on a non-magnetic support, and a lubricant layer over the magnetic layer. The lubricant layer includes a compound selected from the group consisting of hydrocarbyl-substituted cyclopentanes, hydrocarbyl-substituted cyclopentenes, hydrocarbyl-substituted cyclopentadienes, and mixtures or derivatives thereof. The lubricant layer also may be used on a magnetic head for reading and writing information on a magnetic recording medium. The magnetic recording medium and the magnetic head may be used to manufacture computer disk drives, compact disk drives, audio equipment, and video equipment.

40 Claims, 4 Drawing Sheets

U.S. PATENT DOCUMENTS

| | | |
|---|---|---|
| 5,128,216 A | 7/1992 | Ng |
| 5,144,095 A | 9/1992 | Venier et al. |
| 5,162,163 A | 11/1992 | Ohta et al. |
| 5,310,439 A | 5/1994 | Matsui et al. |
| 5,525,392 A | 6/1996 | Baum et al. |
| 5,541,351 A | 7/1996 | Patsidis et al. |
| 5,578,237 A | 11/1996 | Emert et al. |
| 5,578,741 A | 11/1996 | Frey et al. |
| 5,677,051 A | 10/1997 | Ueda et al. |
| 5,776,602 A | 7/1998 | Ueda et al. |
| 5,821,027 A | 10/1998 | Landry-Coltrain et al. |
| 5,874,169 A | 2/1999 | Falcone |

OTHER PUBLICATIONS

A.J. Gellman, Lubricants and overcoats for magnetic storage media, Colloid & Interface Science, vol. 3, pp. 368–372, 1999.

C.M. Mare, Picking the best lube for contact recording, Data Storage, pp 45–49, Jul./Aug. 1997.

M. Yang et al., Cyclotriphosphazenes as Potential Lubricants for Thin Film Hard Disks, Tribology Transactions, vol. 28, No. 3, pp. 636–664, 1995.

S. Mori et al., Tribochemical Reactions at the Head–Disk Interface on Magnetic Recording Media, Proceedings of ASIA TRIB, pp. 300–303, Oct. 12–15, 1998.

Q. Zhao et al., Tribological Study of Phosphazene–Type Additives in Perfluoropolyether Lubricant for Hard Disk Applications, STLE Preprint, No. 98–TC–4C–1, pp. 1–6, 1998.

F.E. Talke, On tribological problems in magnetic disk recording technology, Wear, vol. 190, pp. 232–238, 1995.

C.G. Venier et al., Tris(2–Octyldodecyl)Cyclopentane, a Low Volatility, Wide Liquid–Range, Hydrocarbon Fluid, Unknown Publication, pp. 13.1–1–13.1–12.

E.W. Casserly et al., Tribologically Relevant Properties of Multyply–Alkylated Cyclopentanes. The Design of a Hydrocarbon Molecule for Aerospace Applications, Symposium on Chem. Lub. and Lubrication, American Chem Society, Boston, vol. 35, No. 2, pp. 265–271, Apr. 22–27, 1990.

G.G. Venier et al., Multiply–Alkylated Cyclopentanes (MACs): A New Class of Synthesized Hydrocarbon Fluids, Lubrication Engineering, vol. 47, No. 7, pp. 586–591, 1991.

G.G. Venier et al., Preparation of a New Class of Synthetic Lubricants, Multiply–Alkylated Cyclopentanes (MACs), Symposium on Chem. Lub. and Lubricants, American Chem. Society, Boston, vol. 35, No. 2, pp. 260–264, Apr. 22–27, 1990.

Vasil'ev et al., Compounds with an Herbal Odor VI.* The E Isomers of the Structural Analogs of Leaf Alcohol, *Russian J. of Org. Chem.*, vol. 30, No. 6, pp. 870–875, 1994.

Al–Qualff et al., Metal (IV) phosphate catalysed retro–Prins reaction involving an exetane intermediate, *J. Chem. Soc., Perkin Trans. 2*, pp. 1421–1423, 1999.

Bartlett et al., Nucleophilic Reactivity of the Carbon–Carbon Double Bond. II. Solvolytic Ring Closure of 2–(3–Methyl– and 3,4 dimethyl $-\Delta^3$–cyclopentenyl)ethyl ρ–Nitrobenzenesulfonates, *J. of Am. Chem. Soc.*, vol. 87, No. 6, pp. 1297–1307, 1965.

Vasil'ev et al., Compounds with a Herbal Odor II.* CIS–1–(2–Hydroxyethyl)–2–Ethylcycloalkanes and Their Analogs, *J. of Org. Chem. of U.S.S.R.*, vol. 27, No. 2, pp. 273–278, 1991.

Suzuki et al., Vinylic Organoboranes. 1. A Convenient Synthesis of Acetylenes via the Reaction of Lithium (1–Alkynyl) organoborates with Iodine, *J. Org. Chem.*, vol. 51, No. 24, pp. 4507–4511, 1986.

Aldridge et al., Metabolites of Lasiodiplodia theobromae, *J. Chem. Soc, Sect. C: Organic Chem.*, pp. 1623–1627, 1971.

Boatto et al., Amides and Formamidines with Antinociceptive Activity, *Farmaco*, vol. 48, No. 9, pp. 1279–1289. 1993.

*Aldrich Catalogue Nederland*, Cyclopentene, p. 377, 1992.

*Merck Index $11^{th}$ Ed.*, Cyclopentadiene and Cyclopentane, p. 2741, 1989.

Shawe et al., Iterative Reductive Alkylation Approach to Alkaloids: A Synthesis of (±)–Monomorine I and Its C–3 Epimer, *J. Org. Chem.*, vol. 59, pp. 5841–5842, 1994.

Hutchins et al., Stereoselective Reductions of Substituted Cyclohexyl and Cyclopentyl Carbon–Nitrogen π Systems with Hydride Reagents, *J. Org. Chem.*, vol. 48, No. 20, pp. 3412–3422, 1983.

Ayerst et al., cis– and trans–3: 4–cyclo Pentanopiperidine, *J. Chem. Soc.*, pp. 4097–4104, 1958.

Masse et al., Lewis Acid–Mediated Carbocyclization Reactions of Chiral (E)–Crotylsilanes, *J. Org. Chem.*, vol. 62, No. 26, pp. 9335–9338, 1997.

Fraenkel et al., Structure and Dynamic Behavior of Crowded Cis Vicinal [(N,N–Dimethylamino)cyclopentyl] trimethylammonium Salts and Related Compounds, *J. Am. Chem. Soc.*, vol. 118, No. 50, pp. 12804–12811, 1996.

Snowden et al., Dienamines as Diels–Alder Dienes. An Efficient Cyclohexannulation Sequence, *Tetrahedrom Letters*, vol. 27 No. 6, pp. 699–702, 1986.

Suemune et al., Conversion of Limonene to Prostanoic Acid and 8–Isoprostanoic Acid, *Chem. Pharm. Bull.*, vol. 34, No. 2, pp. 550–557, 1986.

Gustavsson et al., Enantiomers of Cis– and Trans–3–(4–propyl–cyclopent–2–enyl) Propyl Acetate. A Study on the Bioactive Conformation and Chiral Recognition of a Moth Sex Pheromone Component, *Bioorg. Med. Chem.*, vol. 5, No. 12, pp. 2173–2183, 1997.

Fujisawa et al., The Regiospecific Sysnthesis of Vicinally Dialkylated Cyclopentadienes and Its Application to a Synthesis of Allethrolone, *Chem. Letters.*, No. 9, pp. 943–946, 1976.

Kramp et al., Synthesis of Enantiomerically Pure ent–Multifidene and Related Compounds, *J. Chem. Soc, Chem. Conn.*, No. 6, pp. 551–552, 1993.

Search Report, Sep. 8, 2000.

Derwent Transaction of FR 2559606A (Derwent Acc. No. 1985–238531).

Encyclopedia of Chemical Technology, $4^{th}$ Ed., vol. 15, pp. 485–486, 1995.

* cited by examiner

LUBRICANT FOR MAGNETIC RECORDING MEDIUM AND USE THEREOF

CROSS REFERENCE TO RELATED APPLICATIONS

The application claims priority to U.S. patent application Ser. No. 09/534,282, filed Mar. 24, 2000, and Provisional Application Ser. No. 60/126,372, filed on Mar. 26, 1999 entitled "Lubricant for Magnetic Recording Medium and Use Thereof".

FEDERALLY SPONSORED RESEARCH STATEMENT

Not applicable.

REFERENCE TO MICROFICHE APPENDIX

Not applicable.

FIELD OF THE INVENTION

The invention relates to a method of manufacturing a magnetic recording medium having a lubricant film formed thereon. Furthermore, the invention also relates to a data recording/retrieval device which incorporates such magnetic recording media.

BACKGROUND OF THE INVENTION

Thin-film magnetic recording disks and disk drives are commonly used for storing a large amount of data in magnetizable form. Over the last decade, magnetic recording has become the predominant technology for the storage of digital information in modern computer systems.

Magnetic recording generally is accomplished by the relative motion between a magnetic medium and a magnetic recording head. A magnetic recording head consists of a small electromagnet with a gap facing the magnetic medium. During writing, a current is applied to the windings of the electromagnet, thus creating a fringing field at the head gap and magnetizing the magnetic medium according to the direction of the current applied to the head. During reading, the flux from the magnetic medium is intercepted from the head core, inducing a voltage pulse in the coil of the read head.

FIGS. 1A and 1B illustrate a typical disk drive. FIG. 1A is a top plan view of the disk drive, and FIG. 1B is a side view of the disk drive. The disk drive 10 generally includes a magnetic disk 11 and a disk head 16 for writing and reading information to and from the magnetic disk 11. The disk head 16 may include a read/write element 12 and a slider 13. The disk head 16 is connected to a suspension arm 14, which is, in turn, connected to a rotary actuator 15.

A common method to store or retrieve data is called contact start/stop (also known as "CSS"). In a typical CSS operation, the disk head and the surface of the magnetic disk are set so that they are in contact with each other at the start of the operation. Thereafter, a space of an air layer is formed between the head and the surface of the magnetic disk by giving a predetermined rotation to the magnetic disk. In this state, recording or reproduction of data is performed. At the end of the operation, the rotation of the magnetic disk is stopped. At this point, the head and the surface of the magnetic disk are in a frictional contact state as when the operation is started. The frictional force produced between the head and the magnetic disk in this frictional contact state wears the head and the magnetic disk. Eventually, this frictional force may damage the head and the magnetic disk. Furthermore, in the frictional contact state, a slight change in altitude of the head sometimes renders the load on the head non-uniform, thus resulting in damage to the head and the surface of the magnetic disk.

To prevent the wear of the magnetic disk caused by the contact with and sliding on the head, a lubricant layer is provided on the surface of the magnetic disk. A common lubricant used in magnetic disks is perfluoropolyether ("PFPE"). To increase the wear resistance of the magnetic disk and to protect the magnetic material from the corrosive effect of the PFPE lubricant, a protective layer is sometimes provided between the magnetic medium and the lubricant layer. The protective layer may include amorphous carbon, diamond-like carbon, and other materials.

Due to the prevalent use of computers, increases in the areal data storage density of a magnetic disk have continued rapidly and unabatedly for almost 40 years. The trend towards high recording densities is expected to continue. For example, the current areal density is about 0.5 gigabytes per square inch. The next generation disks are going to have an areal density of about 10 gigabytes per square inch. In a few years, the areal density is expected to exceed 40 gigabytes per square inch. To achieve a high recording density, the magnetic head should be positioned as close as possible to the surface of the magnetic medium. The distance between the tip of the magnetic head and the surface of the magnetic medium is referred to as "flight height." For example, to achieve an areal density of about 0.5 gigabytes per square inch, a flight height in the range of about 25–30 nm is required. To achieve an areal density of 10 gigabytes per square inch, the flight height should be decreased to about 10–15 nm. If an areal density of 40 gigabytes per square inch is desired, the flight height should be further decreased to about 3.5 nm. This means that the thickness of the lubricant layer (or film) and the thickness of the protective layer should sum to about 3 nm or less. Consequently, the reliability of the head-disk interface becomes more dependent on the life and performance of the lubricant film as the conquest for higher density disks continues. In other words, the characteristics of the lubricant film, such as its physical, chemical, and tribological properties, have a critical impact on the performance of such high density disks.

First, the lubricant film or layer should last for the lifetime of the drive. If the lubricant layer wears away prematurely, the disk drive would fail accordingly. Furthermore, the lubricant layer should be resistant to chemical degradation. Chemical degradation of the lubricant layer can be induced by thermal decomposition, catalytic reaction with solid surfaces, and mechanical shearing due to high-speed contact with the disk head.

In addition to chemical stability, a major challenge in developing disk lubricant systems is to provide adequate durability without increasing stiction to unacceptable levels. During the lifetime of a magnetic disk, the disk head goes through thousands stop-and-start cycles. If the static friction forces between the disk head and the magnetic medium becomes too large, the drive motor may not develop sufficient torque to restart disk spinning. This may lead to failure of the disk drive.

As mentioned above, PFPEs have been used extensively to form a lubricant film in a magnetic recording medium. PFPEs are relatively expensive. Therefore, cheaper alternatives are more desirable. Although PFPEs have good thermal stability, they decompose readily when they are in contact with Lewis acids. This is an important consideration because the head often is fabricated from an $Al_2O_3$/TiC composite, and $Al_2O_3$ can be converted to $AlF_3$, a strong Lewis acid. This formation of $AlF_3$ leads to chemical degradation of PFPE lubricants. Moreover, use of chlorofluorohydrocarbons ("CFCs") as solvent generally is involved when PFPEs are applied to a magnetic medium. CFCs have detrimental effects on the ozone layer, and use thereof should be avoided, if possible.

In view of the foregoing discussion, in order to meet the challenge of the information age, there is a need to develop magnetic recording media with a lubricant layer that is more chemically and mechanically robust to withstand high shear rates and harsh environments. The lubricant layer should allow decreased flight height so that higher areal densities may be achieved. Furthermore, it is desirable that such lubricant be relatively inexpensive, and that no CFCs be used in forming the lubricant layer.

SUMMARY OF THE INVENTION

The above need is met by a class of hydrocarbyl-substituted cyclopentenes, hydrocarbyl-substituted cyclopentanes, hydrocarbyl-substituted cyclopentadienes, and mixtures or derivatives thereof which may be used to form a lubricant layer over a magnetic layer in a magnetic recording medium.

In one aspect, the invention relates to a magnetic recording medium. The magnetic recording medium includes: (1) a non-magnetic substrate; (2) a magnetic layer formed on the substrate; (3) a lubricant layer over the magnetic layer, where the lubricant layer includes a compound selected from the group consisting of hydrocarbyl-substituted cyclopentanes, hydrocarbyl-substituted cyclopentenes, hydrocarbyl-substituted cyclopentadienes, and mixtures or derivatives thereof. In some embodiments, the magnetic recording medium may further include a protective layer, such as a carbon overcoat, between the magnetic layer and the lubricant layer. In other embodiments, the hydrocarbyl substituent on the cyclopentane, cyclopentene, and cyclopentadiene may include one or more functional groups, such as hydroxy, carboxylic acid, amine, carboxylic ester, carboxylic amide, phosphate, or sulfur-containing compounds, etc.

In another aspect, the invention relates to a magnetic head. The head includes: (1) a head body; and (2) a lubricant layer over at least a portion of the head body, where the lubricant layer includes a compound selected from the group consisting of hydrocarbyl-substituted cyclopentanes, hydrocarbyl-substituted cyclopentenes, hydrocarbyl-substituted cyclopentadienes, and mixtures or derivatives thereof. In some embodiments, the hydrocarbyl substituent on the cyclopentane, cyclopentene, and cyclopentadiene may include one or more functional groups, such as hydroxy, carboxylic acid, amine, carboxylic ester, carboxylic amide, phosphate, or sulfur-containing compounds, etc.

Additional aspects of the invention are described herein. Advantages and objects of the invention are apparent from the following description.

DETAILED DESCRIPTION OF EMBODIMENTS OF THE INVENTION

Figure 1A:
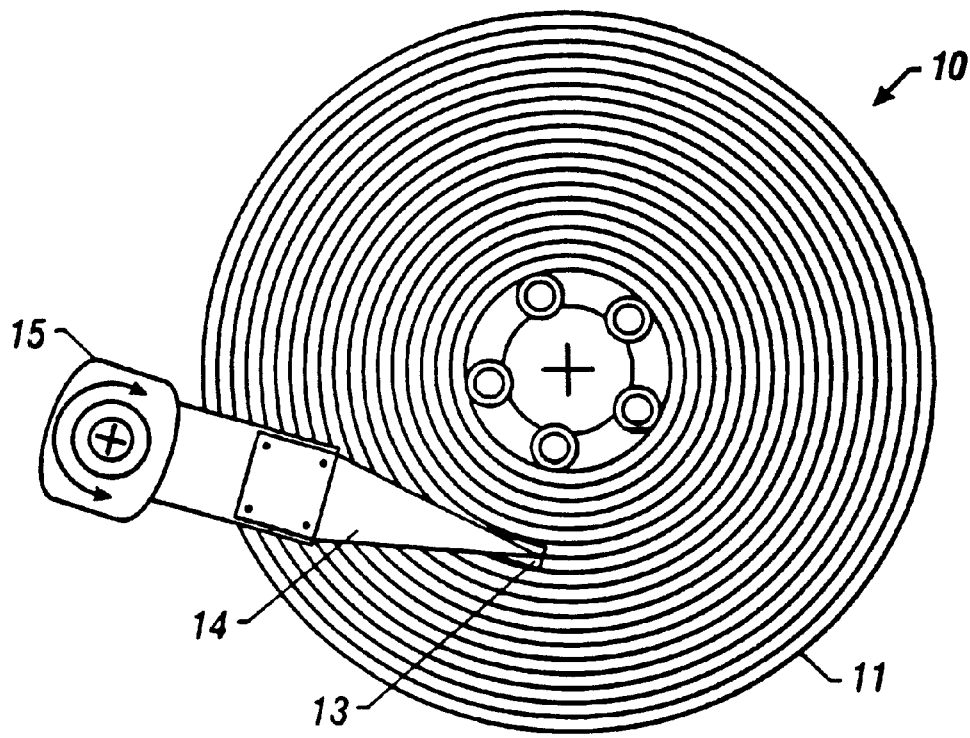
FIG. 1A is a schematic showing the top plan view of a typical computer disk drive system.
Figure 1B:
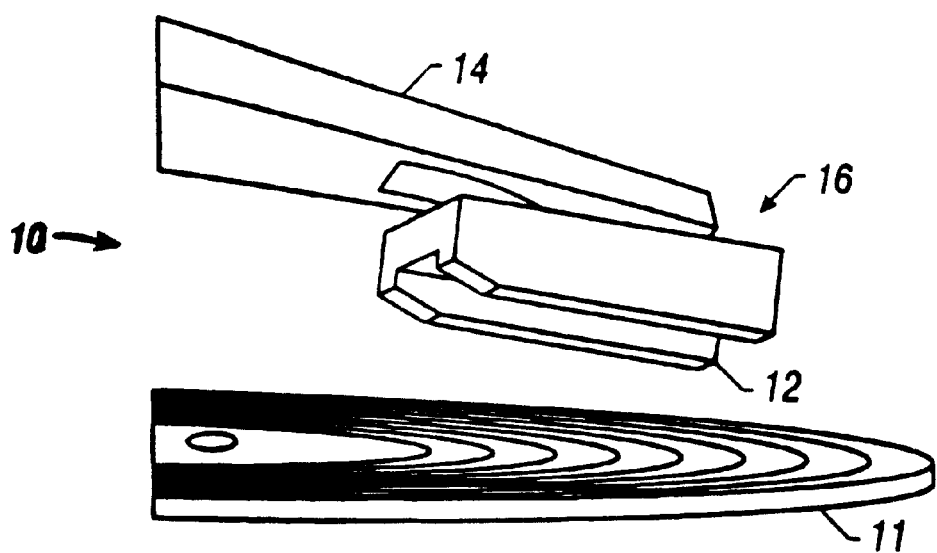
FIG. 1B is a schematic showing a side view of the computer disk drive system of FIG. 1A.

Embodiments of the invention provide a magnetic recording medium with a lubricant film or layer formed from a class of hydrocarbyl-substituted cyclopentadienes, hydrocarbyl-substituted cyclopentenes, hydrocarbyl-substituted cyclopentanes, and mixtures or derivatives thereof. This class of compounds also may be used as a lubricant layer on a magnetic head for reading and writing on a magnetic recording medium. The magnetic recording medium, the magnetic head, or both are useful in manufacturing data recording/retrieval devices, such as a computer disk drive.

Although "hydrocarbyl" is generally understood to mean an organic group that includes only carbon and hydrogen, the term is used herein to refer to both functionalized hydrocarbyl and non-functionalized hydrocarbyl. Functionalized hydrocarbyl refers to an organic group that includes carbon, hydrogen, and a functional group (e.g., a polar group), whereas non-functionalized hydrocarbyl refers to an organic group that includes only carbon and hydrogen. A derivative of a hydrocarbyl-substituted cyclopentane refers herein to any compound that is derived from the hydrocarbyl-substituted cyclopentane. Derivation may occur on the hydrocarbyl or the cyclopentane group. Preferably, derivation should occur on one or more of the hydrocarbyl groups by introducing one or more polar groups. The derivation may be achieved either before or after the hydrocarbyl-substituted cyclopentane is prepared. A derivative of hydrocarbyl-substituted cyclopentadienes and hydrocarbyl-substituted cyclopentenes is similarly defined herein.

Since a lubricating film on a magnetic recording medium is exposed to atmospheric conditions and is applied only once during the manufacturing process, the lubricant in the form of a film over a magnetic recording medium preferably should have low vapor pressure, high chemical stability, and good load-carrying capability, and desirable tribological properties. Substituted cyclopentanes, cyclopentenes, and cyclopentadienes possess the requisite properties for use as a lubricant film or layer in a magnetic recording medium. Some embodiments utilize oligomeric cyclopentane, cyclopentene, and cyclopentadiene derivatives prepared by reacting cyclopentadienes or alkyl-substituted cyclopentadienes with polyhydric alcohols followed by hydrogenation, if appropriate.

Lubricants

As mentioned above, suitable compounds for forming a lubricant layer or film over a layer of magnetic material includes hydrocarbyl-substituted cyclopentanes, hydrocarbyl-substituted cyclopentenes, hydrocarbyl-substituted cyclopentadienes, and mixtures or derivatives thereof. These compounds are selected because they have low vapor pressure and desired tribological properties. For example, tris-(2-octyldodecyl) cyclopentane has a vapor pressure of about $1 \times 10^{-12}$ Torr at about 20° C. Its tribological properties are better or comparable to some of the existing lubricants for magnetic recording media. In addition, it has good thermal stability, additive solubility, and oxidation resistance.

Suitable hydrocarbyl-substituted cyclopentanes generally have the following formula:

where $R_1$ and $R_2$ are hydrocarbyl groups, respectively, m and n are zero or positive integers, respectively. Preferably, the sum of m and n should be less than 6, although compounds with m+n exceeding six are also suitable in embodiments of the invention. It should be understood that either or both $R_1$ and $R_2$ may be further derivatized to include any polar groups.

Suitable hydrocarbyl-substituted cyclopentenes generally have the following formula:

where $R_1$ and $R_2$ are hydrocarbyl groups, respectively, m and n are zero or positive integers, respectively. Preferably, the sum of m and n should be less than 6, although compounds with m+n exceeding six are also suitable in embodiments of the invention. It should be understood that the double bond can be located any where in the ring. Furthermore, either or both $R_1$ and $R_2$ may be further derivatized to include any polar groups.

Suitable hydrocarbyl-substituted cyclopentadienes have the following formula:

where $R_1$ and $R_2$ are hydrocarbyl groups, respectively, m and n are zero or positive integers, respectively. Preferably, the sum of m and n should be less than 6. Either or both $R_1$ and $R_2$ may be further derivatized to include any polar groups.

It should be understood that any one of the compounds represented by the above formulas may be used alone or in combination with another compound or an additive. Methods for synthesizing these compounds have been disclosed in the following patents: (1) U.S. Pat. No. 4,721,823; (2) U.S. Pat. No. 4,849,566; (3) U.S. Pat. No. 4,929,782; (4) U.S. Pat. No. 5,012,022; (5) U.S. Pat. No. 5,012,023; and (6) U.S. Pat. No. 5,144,095. The disclosures of all of the above patents are incorporated by reference in their entirety herein.

In preferred embodiments, $R_1$ is an alkyl group of one to thirty-six carbon atoms. $R_2$ is also a hydrocarbyl group containing from one to about thirty-six carbon atoms. $R_1$ and $R_2$ may the same or different hydrocarbyl groups. Preferably, they are a straight or branched alkyl group of four to 36 carbon atoms. For example, $R_1$ and $R_2$ may be selected from the following hydrocarbyl groups: methyl, ethyl, propyl, n-butyl, n-hexyl, n-octyl, n-decyl, n-dodecyl, n-tetradecyl, iso-dodecyl, iso-tridecyl, 2-ethyl-1-hexyl, 2-octyl-1-dodecyl, 2-decyl-1-tetradecyl, 2-octyl, and t-butyl. It should be noted that the term "hydrocarbyl" used herein includes, but is not limited to, the above examples.

Preferably, m is 0, 1, 2, or 3, although it may be any other positive integers. Preferably, n is an integer ranging from two to six, although it may be 0 or any other positive integers. Preferably, the sum of m and n should not be greater than six, although compounds with m+n exceeding six are also suitable in embodiments of the invention.

The following is a list of preferred cyclopentanes, cyclopentenes, and cyclopentadienes suitable for use as a lubricant in magnetic recording media. It should be understood that the following compounds are merely exemplary and are not intended to limit the scope of the invention as otherwise described herein.

Non-limiting examples of suitable cyclopentanes include: Tri-n-octyl cyclopentane; Tetra-n-octyl cyclopentane; Penta-n-octyl cyclopentane; Tri-n-nonyl cyclopentane; Tetra-n-nonyl cyclopentane; Penta-n-nonyl cyclopentane; Tri-n-decyl cyclopentane; Tetra-n-decyl cyclopentane; Penta-n-decyl cyclopentane; Tri-n-undecyl cyclopentane; Tetra-n-undecyl cyclopentane; Penta-n-undecyl cyclopentane; Tri-n-dodecyl cyclopentane; Tetra-n-dodecyl cyclopentane; Penta-n-dodecyl cyclopentane; Tri-2-ethylhexyl cyclopentane; Tetra-2-ethylhexyl cyclopentane; Di-n-oxtyl, n-decyl cyclopentane; n-octyl, di-n-decyl cyclopentane; Trioctyl, n-decyl cyclopentane; Di-n-octyl, di-n-decyl cyclopentane; n-octyl, tri-n-decyl cyclopentane; Tri-n-tridecyl cyclopentane; Tetra-n-tridecyl cyclopentane; Penta-n-tridecyl cyclopentane; Di-(2-octyl-1-dodecyl)cyclopentane; Tris-(2-octyl-1-dodecyl)cyclopentane; and Tetra-(2-octyl-1-dodecyl) cyclopentane.

Non-limiting examples of suitable cyclopentenes include: Tri-n-octyl cyclopentene; Tetra-n-octyl cyclopentene; Penta-n-octyl cyclopentene; Tri-n-nonyl cyclopentene; Tetra-n-nonyl cyclopentene; Penta-n-nonyl cyclopentene; Tri-n-decyl cyclopentene; Tetra-n-decyl cyclopentene; Penta-n-decyl cyclopentene; Tri-n-undecyl cyclopentene; Tetra-n-undecyl cyclopentene; Penta-n-undecyl cyclopentene; Tri-n-dodecyl cyclopentene; Tetra-n-dodecyl cyclopentene; Penta-n-dodecyl cyclopentene; Tri-2-ethylhexyl cyclopentene; Tetra-2-ethylhexyl cyclopentene; Di-n-octyl, n-decyl cyclopentene; n-octyl, di-n-decyl cyclopentene; Trioctyl, n-decyl cyclopentene; Di-n-octyl, di-n-decyl cyclopentene; n-octyl, tri-n-decyl cyclopentene; Tri-n-tridecyl cyclopentene; Tetra-n-tridecyl cyclopentene; Penta-n-tridecyl cyclopentene; Di-(2-octyl-1-dodecyl)cyclopentene; Tris-(2-octyl-1-dodecyl)cyclopentene; and Tetra-(2-octyl-1-dodecyl) cyclopentene.

Non-limiting examples of suitable cyclopentadienes include: Tri-dodecyl cyclopentadiene; Tetra-dodecyl cyclopentadiene; Penta-dodecyl cyclopentadiene; Penta-n-butyl cyclopentadiene; Penta-n-octyl cyclopentadiene; Penta-n-nonyl cyclopentadiene; Penta-n-decyl cyclopentadiene; Di-n-octyl, n-decyl cyclopentadiene; n-octyl, di-n-decyl cyclopentadiene; Trioctyl, n-decyl cyclopentadiene; Di-n-octyl, di-n-decyl cyclopentadiene; n-octyl, tri-n-decyl cyclopentadiene; Tetra-n-tridecyl cyclopentadiene; Penta-n-tridecyl cyclopentadiene; Di-(2-octyl-1-dodecyl)cyclopentadiene; Tris-(2-octyl-1-dodecyl) cyclopentadiene; Tetra-(2-octyl-1-dodecyl)cyclopentadiene; Di-n-octyl-Tri-n-decyl cyclopentadiene; Tri-n-octyl-Di-n-decyl cyclopentadiene; Methyl-n-octyl-n-decyl cyclopentadiene; Methyl-Di-n-octyl-n-decyl cyclopentadiene; Methyl-Tri-n-octyl-n-decyl cyclopentadiene; Methyl-n-octyl-di-n- decyl cyclopentadiene; Methyl-n-octyl-tri-n-decyl cyclopentadiene; Dimethyl-n-octyl-n-decyl cyclopentadiene; Dimethyl-di-n-octyl-n-decyl cyclopentadiene; Dimethyl-n-octyl-di-n-decyl cyclopentadiene; n-nonyl-n-decyl-n-undecyl cyclopentadiene; Di-n-nonyl-n-decyl-n-undecyl cyclopentadiene; n-nonyl-di-n-decyl-n-decyl cyclopentadiene; and n-nonyl-n-decyl-di-n-undecyl cyclopentadiene.

Derivatized cyclopentanes, cyclopentenes, and cyclopentadienes may be represented by the following formulas:

1. Derivatized Cyclopentanes

2. Derivatized Cyclopentenes

3. Derivatized Cyclopentadienes

wherein $R'_1$ and $R'_2$ are hydrocarbyl groups which may or may not be derivatized respectively; m and n are zero or positive integers (such as 1, 2, 3, 4, 5, . . . ), respectively. Preferably, the sum of m and n should be less than 6. When $R'_1$ or $R'_2$ is a derivatized hydrocarbyl group, it may include, but not limited to, the following functional groups: —OH; —NH$_2$; carboxylic acid; carboxylic ester; phenolic ester; polyether; amide; amine; sulfonamide; thiophosphate; and phosphate.

For example, a cyclopentane, cyclopentene, or cyclopentadiene which includes a polyether or a hydroxyl group may be represented by the following formulas:

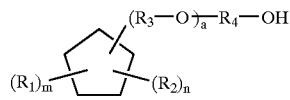

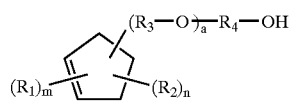

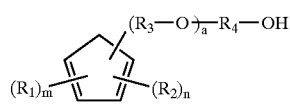

wherein a is any integer, such as 0, 1, 2, 3, 4, 5, 6, 7, 8, 9, or 10; m and n can be zero or any positive integers; Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group.

A cyclopentane, cyclopentene, or cyclopentadiene which includes a phosphate or thiophosphate group may be represented by the following formulas:

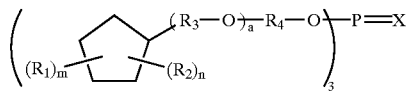

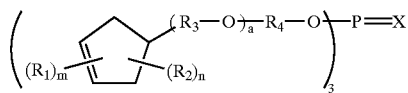

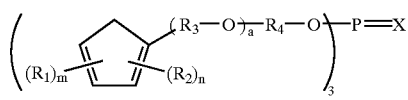

wherein a is any integer, such as 0, 1, 2, 3, 4, 5, 6, 7, 8, 9, or 10; m and n can be zero or any positive integers; Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; X is either oxygen or sulfur.

A cyclopentane, cyclopentene, or cyclopentadiene which includes a carboxylic acid, ester, phenolic ester, or amide group may be represented by the following formulas:

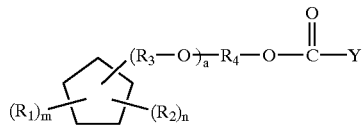

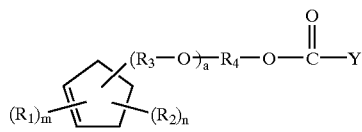

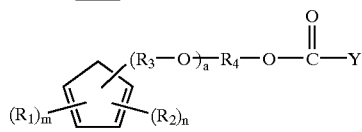

wherein a is any integer, such as 0, 1, 2, 3, 4, 5, 6, 7, 8, 9, or 10; m and n can be zero or any positive integers; Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; Y may be

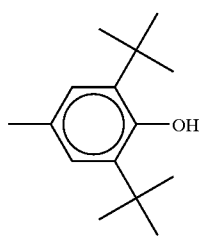

—OH; —NH$_2$; and —(CF$_2$)$_b$—F (in which b is 1, 2, 3, . . . , or 20).

A cyclopentane, cyclopentene, or cyclopentadiene which includes an amine group may be represented by the following formulas:

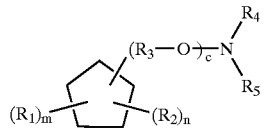

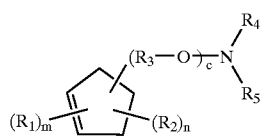

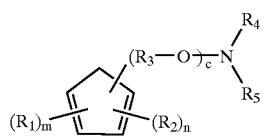

wherein c is any integer, such as 0, 1, 2, 3, 4, 5, 6, 7, 8, 9, or 10; m and n can be zero or any positive integers; Preferably, the sum of m and n should be less than 5, although compounds with m+n exceeding five are also suitable in embodiments of the invention. $R_1$, $R_2$, $R_3$, $R_4$, and $R_5$ are individually a hydrocarbyl group, which may or may not include a polar group; $R_4$ and $R_5$ may also be hydrogen individually.

A cyclopentane, cyclopentene, or cyclopentadiene which includes a sulfonamide group may be represented by the following formulas:

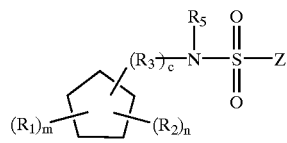

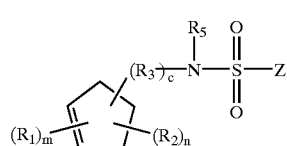

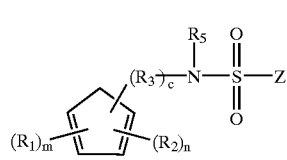

wherein c is any integer, such as 0, 1, 2, 3, 4, 5, 6, 7, 8, 9, or 10; m and n can be zero or any positive integers; Preferably, the sum of m and n should be less than 5, although compounds with m+n exceeding five are also suitable in embodiments of the invention. $R_1$, $R_2$, $R_3$, and $R_5$ are individually a hydrocarbyl group, which may or may not include a polar group; $R_5$ may also be hydrogen; Z may be a hydrocarbyl group or —$(CF_2)_b$—F (in which b is 1, 2, 3, . . . , or 20).

A cyclopentane, cyclopentene, or cyclopentadiene which includes a dimeric amine linkage may be represented by the following formulas:

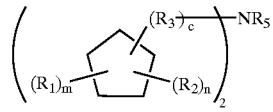

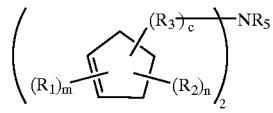

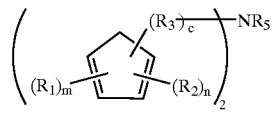

wherein c is any integer, such as 0, 1, 2, 3, 4, 5, 6, 7, 8, 9, or 10; m and n can be zero or any positive integers; preferably, the sum of m and n should be less than 5, although compounds with m+n exceeding five are also suitable in embodiments of the invention. $R_1$, $R_2$, $R_3$, and $R_5$ are individually a hydrocarbyl group, which may or may not include a polar group; $R_5$ may also be hydrogen.

In addition, oligomers of cyclopentanes, cyclopentenes, and cyclopentadienes can also be used in embodiments of the invention, and they may be represented by the following formulas:

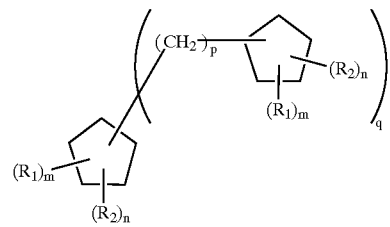

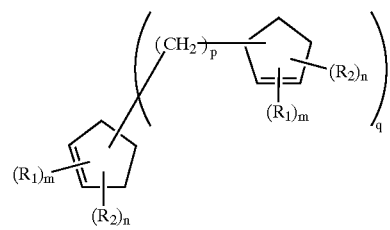

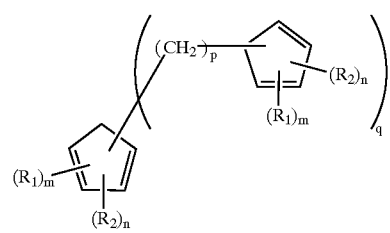

wherein p=1, 2, 3, . . . , or 10; q=1, 2, 3, . . . , or 10; m and n can be zero or any positive integers; preferably, the sum of m and n should be less than 5, although compounds with m+n exceeding five are also suitable in embodiments of the invention. $R_1$ and $R_2$ are individually a hydrocarbyl group, which may or may not include a polar group.

Finally, Diels-Alder derivatives may also be used, and they may be represented by the following formulas:

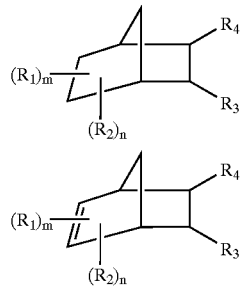

wherein m and n can be zero or any positive integers; preferably, the sum of m and n should be less than 5, although compounds with m+n exceeding five are also suitable in embodiments of the invention. $R_1$ and $R_2$ are individually a hydrocarbyl group, which may or may not include a polar group; $R_3$ and $R_4$ may be a hydrocarbyl, carboxylic acid, carboxylic ester, hydroxy, nitrile, or carboxylic amide. Additional suitable Diels-Alder derivatives that may be used in embodiments of the invention are disclosed by European Patent Applications No. 0 613 886 A1 and No. 0 613 887 A1, both of which were filed on Feb. 25, 1994. The disclosure of these patent applications are incorporated herein by reference in their entirety.

Synthesis of Selected Lubricants

1. Preparation of 3-[tris(2-octyldodecyl) cyclopentadienyl]propionitrile

Tris(2-octyldodecyl)cyclopentadiene (18.12 grams, 20 mmol) was placed in a 3-necked round bottom flask equipped with an additional funnel, a gas inlet adapter, and a septum. After flashing with dried $N_2$ for 2 minutes, 50 ml of dried THF (distilled over K) was added. The solution was cooled in dry ice/acetone bath, followed injected 8.4 M n-butyl lithium in hexane solution (2.40 ml; 20 mmol). The dry ice/acetone bath was removed, and the resulting dark red solution was stirred at room temperature for 1 hour, followed by cooling in dry ice/acetone bath. 3-Bromopropionitrile (2.70 grams, 20 mmol) in 10 ml dried THF solution was then dropwise added from the additional funnel. After the addition, the reaction solution was stirred at room temperature for another 3 hours. The reaction was slowly quenched with 10 ml water. The organic layer was separated, and the aqueous layer was extracted with 50 ml hexane. The organic layers were combined, dried over $MgSO_4$, filtered, and rota-vaporized to give 19.6 grams of yellow liquid. The crude reaction product was purified by column chromatography on $SiO_2$ eluting with 5% ethyl acetate/hexane. The unreacted tris(2-octyldodecyl)cyclopentadiene (3.66 grams) was recovered and the title compound (12.83 grams) was isolated. FTIR: 2248 $cm^{-1}$ (C≡N); $^{13}$C NMR (4 isomers): 152.5–129.1 ppm (C=C), 120.8–119.6 ppm (4 peaks; C≡N), 59.5 ppm, 56.9 ppm, 51.3 ppm, 41.1 ppm, 39.5–26.4 ppm, 22.7 ppm, 14.1 ppm 2. Preparation of Bis-[tris(2-octyldodecyl) cyclopentyl 3-propyl]amine 3-[Tris(2-octyldodecyl)cyclopentadienyl]propionitrile (5.24 grams), palladium 10 wt % on activated carbon (0.1 gram), and 250 ml of heptane were placed in a 500 ml Zipper Clave reactor. Hydrogen was introduced. The hydrogenation was maintained at 700 psi $H_2$, 130° C. for 24 hours. After cooling at room temperature, the catalyst was filtered off, and the solvent was rota-vaporized. The yellow liquid product was chromatographed on $SiO_2$ eluting with 5% ethyl acetate/hexane to give the title compound as a pale yellow viscous liquid (4.33 grams) having a kinematic viscosity of 40 cSt at 100° C., 380 cSt at 40° C., a viscosity index of 155, and $R_f$ (TLC on $SiO_2$, 5% ethyl acetate/hexane) of 0.58. FTIR: 1465 $cm^{-1}$, 1376 $cm^{-1}$, 1307 $cm^{-1}$, 1130 $cm^{-1}$, 721 $cm^{-1}$.

3. Preparation of 3-[tris(2-octyldodecyl)cyclopentyl] propyl Amine

To a stirring solution of 3-[tris(2-octyldodecyl) cyclopentadienyl]propionitrile (8.38 grams; 9.23 mmol) in 20 ml of dried THF was slowly added 1 M lithium alumina hydride in THF solution (9.3 ml) at 0° C. After the addition, the ice bath was removed. The reaction was further stirred at room temperature for 2 hours. The reaction was slowly quenched with 10 ml of water. The reaction mixture solution was extracted with hexane (2×20 ml). The organic layer was dried $MgSO_4$, filtered, and rota-vaporized to yield 8.13 grams, which were further purified by column chromatography on $SiO_2$ eluting with 40% ethyl acetate/hexane to yield 5.21 grams of the title compound: FTIR: 3392 $cm^{-1}$, 1618 $cm^{-1}$, 1074 $cm^{-1}$, 786 $cm^{-1}$, and 721 $cm^{-1}$ (no C≡N at 2248 $cm^{-1}$ was present). $^1$H NMR: δ2.66 (2H); δ1.28; and δ0.90 (t, 18H).

4. Preparation of 2-[2-tris(2-octyldodecyl) cyclopentadienyl ethoxy]ethanol

The hydroxyl group of 2-(2-chchloethoxy)ethanol was protected with 3,4-dihydro-2H-pyran, according to known procedure, to form the corresponding tetrahydropyranyl derivative in 96% yield. The reaction was carried out in methylene in the presence of catalytic amount of p-toluenesulfonic acid.

Tris(2-octyldodecyl)cyclopentadiene (18.12 grams, 20 mmol) was placed in 3-necked round bottom flask equipped with an additional funnel, a gas inlet adapter, and a septum. After flashing with dried $N_2$ for 2 minutes; 50 ml of dried THF was added. The solution was cooled in a dry ice/acetone bath, followed by injecting 8.4 M n-butyl lithium in hexane solution (2.40 ml; 20 mmol). The dry ice/acetone bath was removed, and the resulting dark red solution was stirred at room temperature for 1 hour, followed by cooling in a dry ice/acetone bath. The above tetrahydropyranyl derivative of 2-(2-chchloethoxy)ethanol (4.45 grams, 20 mmol) in 10 ml dried THF was then dropwise added from the additional funnel. After the addition, the reaction solution was stirred overnight at room temperature under $N_2$. The reaction was slowly quenched with 20 ml water. The organic layer was separated, and the aqueous layer was extracted with 50 ml hexane. The organic layers were combined, dried over $MgSO_4$, filtered, and rota-vaporized to give 21.65 grams of liquid. To the liquid was added 20 ml of methylene dichloride and 0.2 ml of concentrated HCl to de-protect the hydroxy group. The reaction mixture was stirred overnight, followed by aqueous work-up to give 19.27 grams of a crude product. The title compound (16.90 grams) was obtained after purification by column chromatography on $SiO_2$, eluting with 5% ethyl acetate/hexane. FTIR: 3471-$cm^{-1}$, 3050-$cm^{-1}$, 1647 $cm^{-1}$, 1618 $cm^{-1}$, 1058 $cm^{-1}$. $^{13}$C NMR (2 isomers): 150.7 ppm, 148.4 ppm, 145.1 ppm, 142.6 ppm, 139.3 ppm, 126.7 ppm, 122.9 ppm, 121.9 ppm, 71.8 ppm, 68.8 ppm, 61.9 ppm, 47.8–26.5 ppm, 22.7 ppm, and 14.1 ppm

5. Preparation of 2-[2-tris(2-octyldodecyl) cyclopentyl]-ethoxy Ethanol

The hydrogenation of 2-[2-tris(2-octyldodecyl) cyclopentadienyl ethoxy]ethanol was carried out in a similar manner as described in Example 2, except the catalyst used was rhodium on alumina.

2-[2-tris(2-octyldodecyl)cyclopentadienyl ethoxy]ethanol (20 grams), rhodium (5% Rh) on alumina (1 gram), and 250 ml of heptane were placed in a 500 ml Zipper Clave reactor. The hydrogenation was maintained at 950 psi $H_2$ and 280° C. for 24 hours. The title compound was further purified by column chromatography on $SiO_2$, eluting with 5% ethyl acetate/hexane, to give 18.59 gram of colorless liquid. FTIR: 3471 $cm^{-1}$, 1120 $cm^{-1}$, 1058 $cm^{-1}$, 890 $cm^{-1}$, 721 $cm^{-1}$. $^1H$ NMR: d 3.70 (1H), d 3.52 (1H), d 3.46 (1H), d 1.25, d 0.87. $^{13}C$ NMR: 71.8 ppm, 70.5 ppm, 61.9 ppm, 52.8–33.7 ppm, 31.9 ppm, 30.3 ppm, 29.8 ppm, 29.5 ppm, 26.7 ppm, 22.7 ppm, and 14.1 ppm.

6. Preparation of 3,5-di-tertiary-butyl 4-hydroxy Benzoic Ester of [2-tris-(2-octyldodecyl) cyclopentyl]-ethoxy Ethanol 2-[2-tris(2-octyldodecyl)cyclopentyl]ethoxy ethanol (8.0 grams, 8.35 mmol), 3,5-di-tert-butyl-4-hydroxybenzoic acid (2.94 grams, 12.6 mmol), and a catalytic amount of p-toluenesulfonic acid in 60 ml toluene were refluxed in a Dean-Stark trap. The reaction was monitored by TLC until all 2-[2-tris(2-octyldodecyl)cyclopentyl]ethoxy ethanol was consumed. It took 4 days to complete the reaction. The reaction solution was washed with 1M aqueous $K_2CO_3$ (2×20 ml). After being dried, filtered, and rota-vaporized, the crude reaction product was chromatographed on $SiO_2$, eluting with 3% ethyl acetate/hexane to yield about 9.87 grams of the pure title compound. The pure title compound was characterized by the following: FTIR: 3635 $cm^{-1}$, 1718 $cm^{-1}$, 1600 $cm^{-1}$. $^1H$ NMR: d 7.92 (s, 2H), d 5.63 (s, 1H), d 4.44 (t, 2H), d 3.74 (t, 2H), d 3.53 (m, 2H), d 1.44 (s, 18H), d 1.22 (br.s.),d 0.91 (t, 18H). $^{13}C$ NMR: 167 ppm, 158.2 ppm, 135.6 ppm, 127.2 ppm, 121.2 ppm, 68.1 ppm, 64.0 ppm, 45.1 ppm, 34.3 ppm, 31.9 ppm, 30.2 ppm, 30.1 ppm, 29.8 ppm, 29.4 ppm, 22.7 ppm, 14.1 ppm.

7. Preparation of Di-(n-decyl)cyclopentane Crosslinked by —$(CH_2)_{10}$— Groups In a one-liter three-necked flask fitted with a mechanical stirrer and a Soxhlet extractor packed with 3A molecular sieves (about 15 g) and topped with a condenser, 25.1 g of di-(n-decyl)cyclopentadiene (73 mmol), 12.6 g of 1,10-decanediol (73 mmol), 5 g of KOH, and 250 g of triglyme were stirred and deoxygenated with a stream of nitrogen. The mixture was then heated to reflux under nitrogen for two hours. The mixture was cooled and washed with water to remove base and triglyme. The product was dried and hydrogenated over palladium on carbon. The resulting product was characterized by gel permeation chromatography to determine the molecular weight. The number average molecular weight was 1250, indicating that on average about 3 di(n-decyl)cyclopentadienes had been crosslinked. The weight average molecular weight of 2250 indicates that molecules containing a higher number of crosslinked di(n-decyl)cyclopentadienes were formed. The measured viscosity at 100°, 40 cSt, is consistent with these high molecular weights.

Magnetic Recording Medium

In accordance with embodiments of the invention, a magnetic recording medium includes: (1) a non-magnetic support; (2) a magnetic layer formed on the support; and (3) lubricant layer over the magnetic layer. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Optionally, there may be a protective layer between the magnetic layer and the lubricant layer. In other words, some embodiments may include a protective layer, while other embodiments may not include such a layer.

In some embodiments, the hydrocarbyl substituent on the cyclopentane, cyclopentene, and cyclopentadiene may be derivatized to include one or more polar groups, such as hydroxy, carboxylic acid, amine, carboxylic ester, carboxylic amide, phosphate, and sulfur compounds. For example, hydroxylated, dihydroxylated, and polyhydroxylated derivatives are preferred. Carboxylic acid derivatives and their salts, amine derivatives, carboxylic ester derivatives, carboxylic amide derivatives, phosphate derivatives, and sulfur compounds derived from multiple-alkylated cyclopentadienes, multiple-alkylated cyclopentenes, and multiple-alkylated cyclopentanes also may be used. These derivative groups, e.g., polar groups, may be incorporated into a multiple-alkylated cyclopentadiene, cyclopentene, or cyclopentane by known chemistries of cyclopentadiene, alkene, diene, and alkane. For example, cyclopentadiene can be made to undergo Diels-Alder reactions and nucleophilic reactions to include derivative groups. These derivative groups may strengthen the bonding between the lubricant film and the surface beneath it.

In addition to a magnetic recording medium, a magnetic head for reading and writing information on the magnetic recording medium also is provided by embodiments of the invention. The magnetic head includes: (1) a head body; and (2) a lubricant layer over at least a portion of the head body. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Similarly, the hydrocarbyl substituents may be derivatized to include one or more polar groups. A data storage/retrieval device may be constructed using either the magnetic head or the magnetic recording medium provided by embodiments of the invention.

Figure 2:
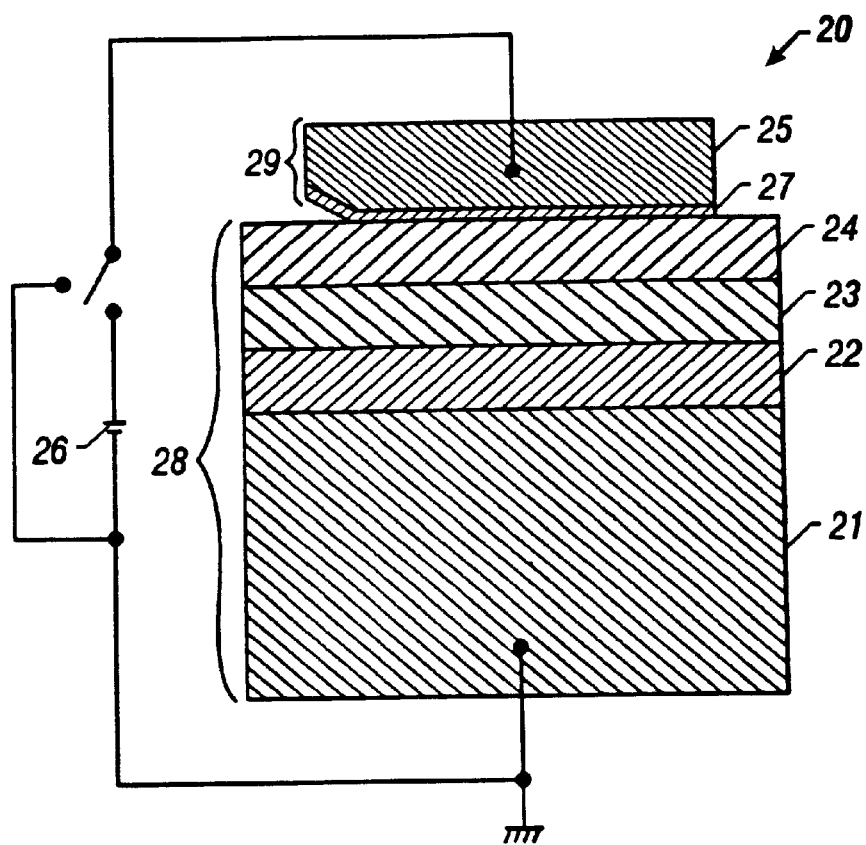
FIG. 2 is a cross-sectional view of a data storage/retrieval device in accordance with an embodiment of the invention.

FIG. 2 illustrates a cross-sectional view of a data storage/retrieval device manufactured in accordance with one embodiment of the invention. It should be understood that the data storage/retrieval device may be used to manufacture computers audio/video equipment, and the like. Typically, a computer includes a central processing unit ("CPU"), a monitor, a keyboard, and a disk drive connected to the CPU. Other components suitable for constructing a computer are known in the art. For example, U.S. Pat. No. 4,620,275 discloses a computer, and the disclosure of this patent is incorporated by reference herein in its entirety.

Referring to FIG. 2, a data storage/retrieval device 20 includes a magnetic recording medium 28, a magnetic head 29, and a power supply 26, which is connected to the magnetic recording medium 28 and the magnetic head 29. The magnetic recording medium 28 is formed by coating a layer of magnetic material 22 on a substrate support 21. Preferably, the layer of magnetic material 22 is protected by a protective layer 23. The lubricant layer 24 is provided on the protective layer 23. The magnetic head 29 includes a body 25 for the head and an insulating layer 27 which is optional. In some embodiments, the magnetic head 29 is coated with a lubricant layer. To operate this data storage/retrieval device, a DC voltage from a power supply 26 preferably is applied across the support 21 and the magnetic head 29.

The magnetic recording medium in accordance with embodiments of the invention may be manufactured by the following method: (1) providing a non-magnetic support; (2) forming a magnetic layer on the support; and (3) forming a lubricant layer over the magnetic layer. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Optionally, a protective layer may be formed between the magnetic layer and the lubricant layer.

Generally, any non-magnetic materials may be used as a substrate support. Suitable materials for the support include, but are not limited to, a metal such as an aluminum alloy, a titanium alloy, or a stainless steel alloy; plastic such as polyester, polyimide, polyamidoimide, polyethersulfone, polysulfone, aromatic polyether, an epoxy resin, a urea resin, a melamine resin, polycarbonate, a diallylphthalate resin, an acrylic resin, a phenolic resin, polyphenylenesulfide, polyphenyleneether, a polyacetal resin, polybutyreneterephthalate, a bismaleimidetriazine resin, a polyoxybenzylene resin, a polyphenylenesulfide; ceramics such as glass, silicon, germanium, alumina, silica, diamond, amorphous carbon, or graphite; and a metal such as an aluminum alloy coated with anodized aluminum, an Ni—P-plating film, Cr, FeNi, stainless steel, Mo. Or W. It should be recognized that a non-magnetic support is not always necessary in manufacturing a magnetic medium.

Any magnetic materials may be used to form the magnetic layer on the support. Suitable magnetic materials include, but are not limited to, an oxide such as $Fe_3O_4$, $g$-$Fe_2O_3$, barium ferrite, or $CrO_2$; a nitride such as $Fe_3N_4$; a carbide such as $Fe_5C_2$; a metal containing cobalt such as Co, CoNi, CoNiP, CoMnP, CoMnNiP, CoRe, CoPt, CoNiPt, CoCr, CoCrTa, CoNiRe, CoMnReP, CoFeCr, CoV, CoRu, CoOs, CoPtCr, CoPtV, CoRh, CoCrRh, CoNiMo, CoNiCr, CoNiW, or CoSm; a metal containing iron such as FeNd, FeMg, FeNd, FeAg, FePd, or FeTb; and a metal containing manganese such as MnAl or MnCuAl. It also is possible to use a resin prepared by mixing and dispersing fine particles of the above various magnetic materials.

Suitable materials for forming the protective layer between the magnetic layer and the lubricant layer include, but are not limited to, a silicon compound such as $SiO_2$, $Si_3N_4$, SiC, or a silicic acid polymer; a metal oxide such as $Al_2O_3$, CoO, $Co_3O_4$, $Co_2O_3$, a $Fe_2O_3$, $Cr_2O_3$, $CrO_3$, $TiO_2$, $ZrO_2$, ZnO, PbO, NiO, $MoO_2$, or $SnO_2$; a metal sulfide such as $MoS_2$, $WS_2$, or $TaS_2$; a metal carbide such as TiC, ZrC, CrC, or TaC; a metal fluoride or graphite fluoride; a metal such as W, Cr, Ir, NiB, NiP, FeCr, NiCr, Sn, Pb, Zn, Tl, Au, Ag, Cu, Ga, Ru, Rb, Mn, Mo, Os, or Ta, or an alloy of each of these metals; a semiconductor such as Si, Ge, B. or C (e.g., amorphous hydrogenated carbon, amorphous nitrogenated carbon, amorphous carbon, diamond-like carbon, or a mixture thereof, or graphite-like carbon or a mixture thereof); and plastic such as polytetrafluoroethylene, a phenolic resin, or polyimide.

Methods for forming these layers are known in the art. For example, these films may be formed by chemical vapor deposition, physical vapor deposition, electrochemical plating, electron-assisted deposition, ion-assisted deposition, and so on.

Suitable materials for making the body of the magnetic head include, but are not limited to, an insulator such as quartz, glass, alumina, sapphire, ruby, diamond, or silicon; silicon carbide having conductivity, a sintered body such as alumina-titanium carbide; and a ceramics-based conductor, such as manganese-zinc ferrite or nickel-zinc ferrite. Optionally, a thin insulating film may be applied to the body of the magnetic head. The insulating film may include diamond-like carbon, $SiO_2$, or alumina. In some embodiments, the magnetic head is coated with a lubricant layer formed from a compound selected from the group consisting of hydrocarbyl-substituted cyclopentane, hydrocarbyl-substituted cyclopentene, hydrocarbyl-substituted cyclopentadiene, and mixtures or derivatives thereof.

While the cyclopentanes, cyclopentenes, and cyclopentadienes may be used alone in a lubricant layer, other lubricants and/or additives also may be used in combination as far as the additional lubricants do not adversely affect the performance of the magnetic recording media. While any known additives may be used, cyclic phosphazenes additives, such as mixtures of fluorinated phenoxy-substituted cyclic phosphazenes or mixtures of fluoroalkoxy substituted cyclic phosphazenes, are preferred. Suitable additional lubricants include, but are not limited to, metallic soaps, fatty acid, amide; fatty acid esters; higher aliphatic alcohols; monoalkyl phosphates; dialkyl phosphates, trialkyl phosphates, paraffins, silicone oils; animal or vegetable oils; mineral oils, higher aliphatic amines, inorganic fine powders, such as graphite, silica, molybdenum disulfide, and tungsten disulfide; resin fine powders, such as polyethylene, polypropylene, polyvinyl chloride, and ethylene vinyl chloride copolymer and polytetrafluoroethylene, alpha-olefin polymers, and unsaturated aliphatic hydrocarbons, which are liquid at room temperature.

Various methods are known in the art for forming a lubricant layer over a magnetic layer. For example, a lubricant film may be formed by coating or spraying a solution of a lubricant in an organic solvent onto a substrate (e.g., a non-magnetic support having thereon a magnetic film) and letting the solvent evaporate. Another method includes rubbing a substrate having a magnetic layer with an object impregnated with a lubricant to transfer the lubricant thereto. Still another method includes immersing a substrate with a magnetic layer in a solution of a lubricant in an organic solution to let the lubricant be adsorbed onto the substrate. Furthermore, the lubricant layer may be formed by the method referred to as the "Langmuir-Blodgett" method. The Langmuir-Blodgett method may be used to construct a monomolecular or multimolecular layer in a film. This method is described generally in U.S. Pat. No. 4,907,038.

In some embodiments, a lubricant layer is formed by dip-coating, coil-bar coating, or gravure coating followed by drying. A variety of solvents may be used in this method, such as ethanol, methanol, benzene, toluene, acetone, cyclohexane, heptane, ethyl ether, dichloromethane, isopropanol, petroleum naphtha, ethyl acetate, methyl ethyl ketone, and so on. Although CFCs and related solvents also may be used, they are not preferred due to their adverse environmental effects.

The following examples are given to illustrate embodiments of the invention and are not intended to limit the scope of the invention as otherwise described. All numbers disclosed herein are approximate values.

EXAMPLE 1

This example demonstrates that Pennzane® X-2000, a lubricant made of tris-(2-octyldodecyl)cyclopentane, has a lower friction coefficient and comparable wear resistance to Z-DOL®, an existing lubricant. Pennzane® X-2000 is a product available from Pennzoil-Quaker State, Inc., Houston, Tex. Z-DOL® is a functionalized PFPE manufactured by Ausimont Montedison.

For comparison, Pennzane® X-2000 and Z-DOL® samples were tested for wear scar. Their friction coefficients also were measured. The tests were conducted in accordance with ASTM D5707-95 and DIN 51 834 methods. A description of the ASTM D5707-95 and DIN 51 834 methods can be found in the article entitled: *New ASTM and DIN Methods for Measuring Tribological Properties Using the SRV® Test Instrument*, printed in *NLGI Spokesman*, Vol. 60, No. 12, page 17 (March 1997). This article is incorporated by reference in its entirety herein.

The test results are summarized in Table I. A number of additives were used with Pennzane® X-2000 and Z-DOL®. They included: tricresyl phosphate; oleic acid; Irgalube 63; Irgalube 232; glycerol monooleate; and Sakura lube 100. Irgalube 63 is an ashless dithiophosphate; Irgalube 232 is ashless butylated triphenyl phosphorothionate; and Sakura lube 100 is molybdenum dithiocarbamate.

TABLE I

| | Friction Coefficient | | | | Wear Scar | |
| | 15 min. | | 120 min. | | (mm) | |
| Additives | Pennzane ® X-2000 | Z-DOL ® | Pennzane ® X-2000 | Z-DOL ® | Pennzane ® X-2000 | Z-DOL ® |
|---|---|---|---|---|---|---|
| Tricresyl Phosphate | 0.096 | 0.125 | 0.108 | 0.122 | 0.56 × 0.59 | 0.61 × 0.68 |
| Oleic acid | 0.114 | 0.112 | 0.142 | 0.100 | 0.90 × 1.01 | 0.86 × 0.89 |
| Ashless dithio-phosphate | 0.097 | 0.128 | 0.083 | 0.117 | 0.73 × 0.75 | 0.63 × 0.66 |
| Ashless butylated triphenyl phosphoro-thionate | 0.101 | 0.127 | 0.094 | 0.130 | 0.51 × 0.49 | 0.92 × 0.95 |
| Glycerol monooleate | 0.118 | 0.116 | 0.099 | 0.113 | 0.86 × 0.86 | 0.87 × 0.92 |
| Molybdenum dithio-carbamate | 0.135 | 0.110 | 0.132 | 0.106 | 0.80 × 0.88 | 0.77 × 0.83 |

It can be seen from Table 1 that the friction coefficients of Pennzane® X-2000 with various additives generally are lower than those of Z-DOL® with the same additives. The wear resistance of Pennzane® X-2000 generally is comparable to or better than that of Z-DOL®.

EXAMPLE 2

This example demonstrates that Pennzane® X-2000 lubricant films formed on a magnetic medium have a longer lifetime in contact-start/stop cycles than Z-DOL® lubricant films.

A number of samples that included a magnetic medium with a lubricant film formed thereon were prepared. Lubricant films of both Pennzane® X-2000 and Z-DOL® were deposited on amorphous hydrogenated carbon overcoated disks. The lubricant films were formed by dipping the magnetic medium into a solution containing the respective compositions at a specified weight percentage. 1,1,2 trichloro-trifluoroethane was used as solvent for Z-DOL®, whereas cyclohexane was used as solvent for Pennzane® X-2000. These samples were tested in an apparatus so called High-Velocity Ball-on-Inclined-Plane ("HVBOIP") tester, which generates tribological conditions similar to the magnetic head/disk interface in a computer disk drive.

Figure 3:
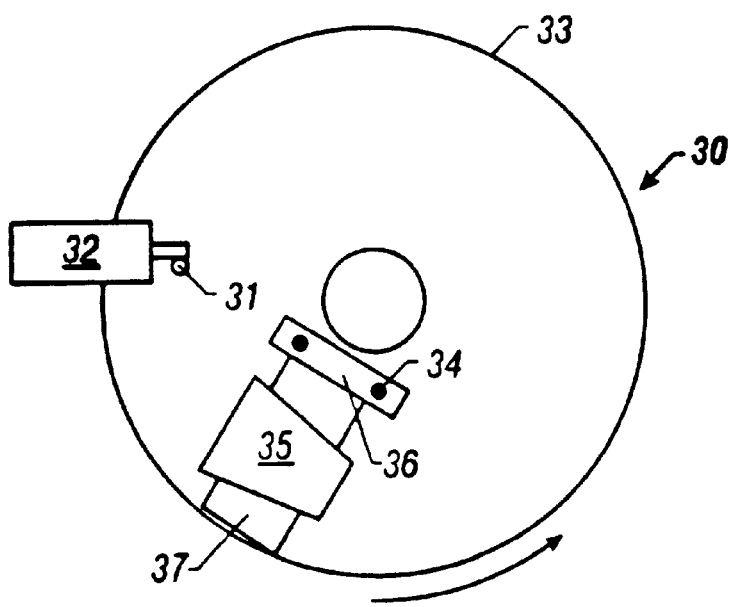
FIG. 3 is a schematic showing the top view of the High Velocity Ball-on-Inclined Plane tester used in an embodiment of the intention.

FIG. 3 shows schematically the top view of the HVBOIP tester 30. Referring to FIG. 3, a ruby ball 31 with a radius of about 1.59 mm is held at one end of a strain gauge 32. The ruby ball is polished by using a diamond paste of 1 micron average particle diameter and has a surface roughness, $R_a$ of about 2.1 nm and a $R_{max}$ of about 19.4 nm. The strain gauge 32 has a force resolution of about 0.1 mN. The test sample is cut from a super-smooth disk (with about 75 Å thick hydrogenated carbon overcoat) and is mounted on another disk. A disk section 35 is glued to a substrate 37, and a substrate clamp 36 is held down by a pair of screws 34.

A spin stand (not shown) is used to rotate the disk. The sample is mounted on the disk using successive applications of a dilute glue solution in a staircase form. The glue controls the angle of inclination. In this way, a 0.001° inclination angle can be achieved. When the test commences, the disk is rotated at a speed of about 2 m/s, and the ball is stationary. For every revolution, the ball slides on the incline plane once at the angle the glue controls. This simulates impact, landing, and take off. Because the angle of inclination increases the test severity, the total number of cycles required to reach failure can be shortened. The test is conducted in a size 10 clean room.

The test procedure is divided into two steps. In the first step, the disk is accelerated to the test speed of about 2 m/s (760 rpm) at about 0.1 second and rotated at the test speed for 100 sliding cycles, and then the test was stopped. The acceleration or deceleration step to the desired speed is accomplished within one rotational cycle, so that the effect on test speed throughout the test is negligible. These 100 cycles constitute a unit test cycle. Because of the high test speed, the data acquisition rate for the test apparatus of 5000 inputs per second is inadequate. Only few data points on the frictional force could be collected.

To correct for this inadequacy, after every 100 high speed test cycles, the second step of the test procedure is applied to examine the surface damage as well as to measure accurately the frictional force. In the second step, the sample is rotated at a very slow speed of about 0.05 m/s (2 rpm). This allows the measurement of the frictional force between the ball and the inclined plane sample and also allows direct observation of the sample surface via a video camera. These two steps are repeated for each unit cycle until the sample failed. The failure of the sample is indicated by a sudden drastic increase in frictional force. The entire test procedure is controlled by a computer.

Figure 4:
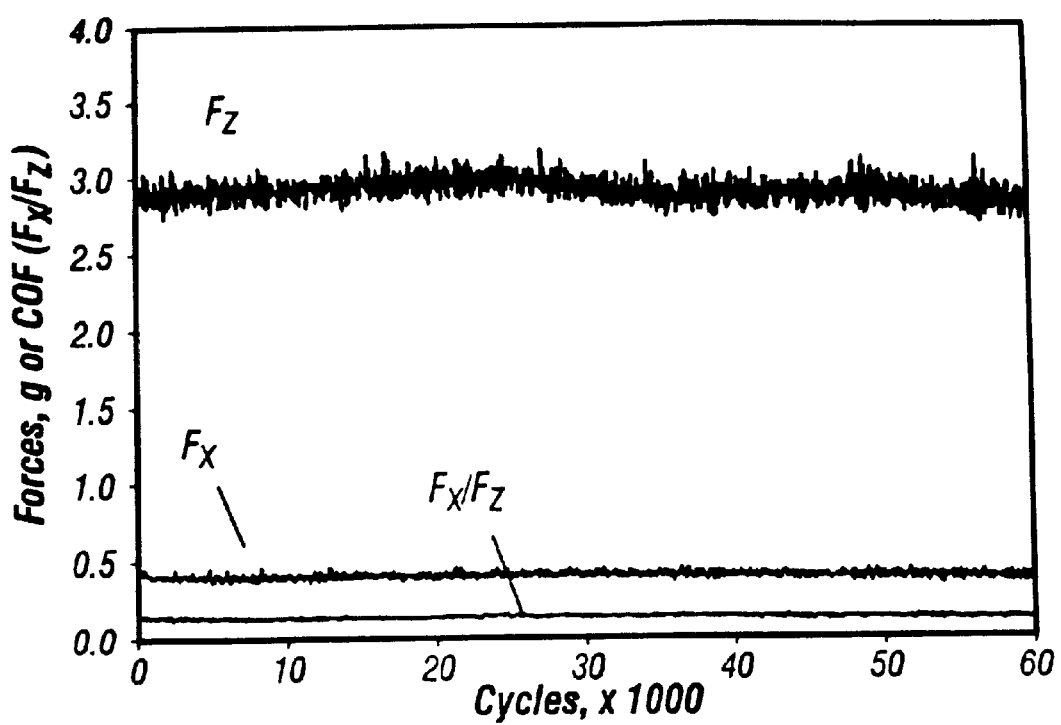
FIG. 4 is a plot of coefficient of friction as a function of number of cycles for Pennzane® Synthesized Hydrocarbon Fluid X-2000 (0.11 wt. %).
Figure 5:
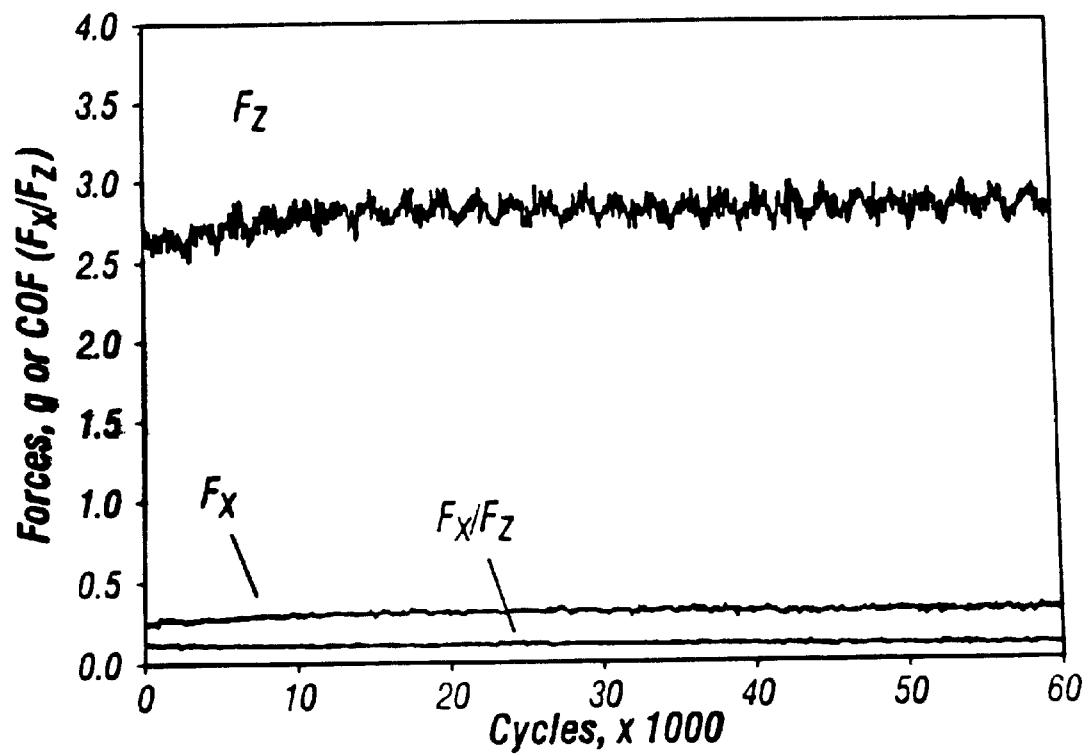
FIG. 5 is a plot of coefficient of friction as a function of number of cycles for Pennzane® Synthesized Hydrocarbon Fluid X-2000 (0.22 wt. %).

Lubricant films were made from a solution containing Pennzane® X-2000 at 0.055 wt. %, 0.11 wt. % and 0.22 wt. % and Z-DOL® at 0.1 wt. %, respectively. These films were tested in the HVBOIP tester. Both normal force $F_z$ and frictional force $F_x$ for each film were measured. The coefficient of friction is the ratio of $F_x/F_z$. FIGS. 4 and 5 are plots for two Pennzane® X-2000 lubricant films. In both figures, normal force $F_z$, frictional force $F_x$, and coefficient of friction $F_x/F_z$ are plotted as a function of the number of cycles. The coefficient of friction for the Pennzane® X-2000 lubricant film with 0.11 wt. % is about 0.4, whereas the coefficient of friction for the Pennzane® X-2000 lubricant films with 0.22 wt. % is decreased to about 0.25.

Figure 6:
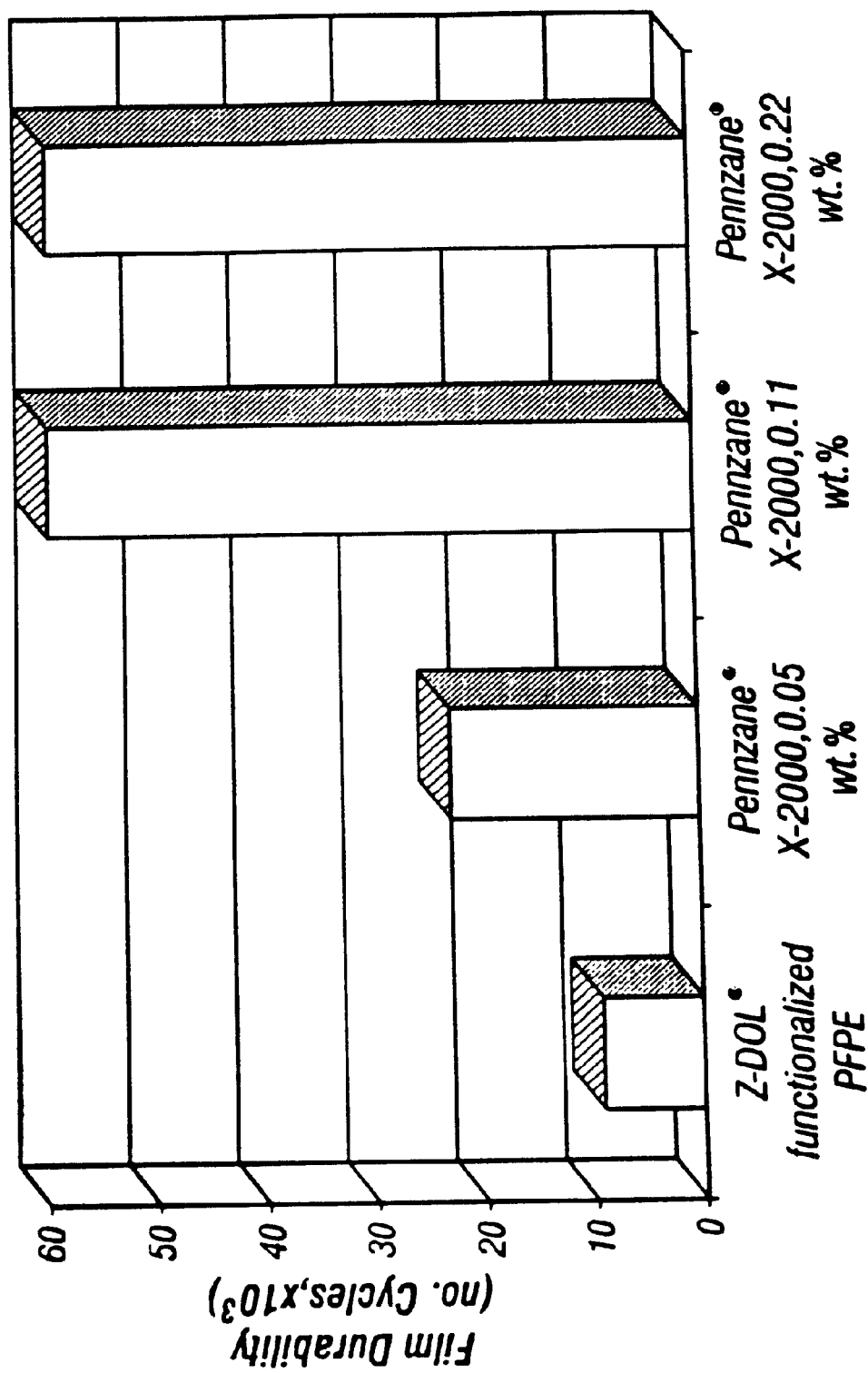
FIG. 6 is a plot which compares film durability of various lubricants.

In addition to the coefficient of friction, the number of cycles to failure was also measured, and the data are present in Table II and FIG. 6. It is notable that the Pennzane® X-2000 lubricant films lasted longer than the Z-DOL® lubricant film. The films made from a solution containing 0.11 wt. % and 0.22 wt. % of Pennzane® X-2000 are at least six times more durable than the Z-DOL® lubricant film. Therefore, disk drives incorporating Pennzane® X-2000 or similar lubricants should have longer lifetime and improved performance.

TABLE II

| Lubricant | Number of Cycles to Failure |
| --- | --- |
| Z-DOL ® (0.1 wt. %) | 8,000 to 10,000 |
| Pennzane ® X-2000 (0.055 wt. %) | 10,000 to 35,000 |
| Pennzane ® X-2000 (0.11 wt. %) | greater than 60,000 |
| Pennzane ® X-2000 (0.22 wt. %) | greater than 60,000 |

As demonstrated above, embodiments of the invention provide a lubricant layer for a magnetic recording medium so that the areal density of such a magnetic recording medium may be increased substantially. The suitable lubricants are less costly than some of the existing lubricants, such as PFPEs. A magnetic recording medium incorporating such a lubricant film makes it possible to manufacture higher-density computer disks, compact disks, audio tapes, and video tapes. Formation of the lubricant films according to embodiments of the invention does not require the use of environmentally-hazardous solvents, such as chlorofluorohydrocarbons. Therefore, embodiments of the invention are more environmentally-friendly than some of the existing methods. Furthermore, the lubricants used in embodiments of the invention are more resistant to chemical degradation that may occur in the data storage/retrieval process. They also have substantially higher additive solubility than PFPEs. Other properties and advantages are apparent to a person of ordinary skill in the art.

While the invention has been described with a limited number of embodiments, modifications and variations therefrom exist. For example, although suitable lubricants are described with respect to hydrocarbyl-substituted cyclopentanes, cyclopentenes, and cyclopentadienes, other derivatives therefrom also may be used to form a lubricant film over a magnetic recording medium. The derivatives may include phenyl substitution, amine substitution, and so on. Furthermore, it is possible to incorporate a polymerizable unit or moiety into the above-described lubricant to render them polymerizable. Moreover, these lubricants may further be functionalized to strengthen the bonding between the lubricant layer and the underneath layer. While the invention is described with reference to a magnetic recording medium, this invention may be applied to any information storage/retrieval system, which requires a lubricant film or layer. Specifically, the invention is not limited to a contact-stop-start information storage/retrieval system. The appended claims are intended to cover all modifications and variations as falling within the scope of the invention.

What is claimed is:

1. A compound represented by one or more of the following formulas:

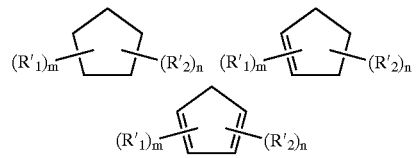

wherein $R'_1$ and $R'_2$ are respectively a hydrocarbyl group which includes a functional group selected from —OH; —NH$_2$; carboxylic acid; phenolic ester; polyether; amide; amine; sulfonamide; thiophosphate; and phosphate, and m and n are respectively zero or a positive integer and wherein m+n is greater than one.

2. The compound of claim 1, where the sum of m and n is a positive integer.

3. The compound of claim 2, where the sum of m and n is 1, 2, 3, 4, 5, or 6.

4. The compound of claim 3, where m is 1, 2, 3, 4, 5, or 6.

5. The compound of claim 3, where n is 1, 2, 3, 4, 5, or 6.

6. The compound of claim 1, wherein the compound is represented by one or more of the following formulas:

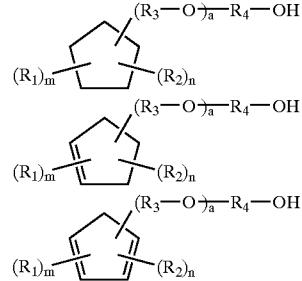

wherein a is 0, 1, 2, 3, 4, 5, 6, 7, 8, 9, or 10; m and n are zero or a positive integer; the sum of m+n is greater than zero; $R_1$, $R_2$, $R_3$, and $R_4$ are individually a hydrocarbyl group.

7. The compound of claim 6, where the sum of m and n is, 1, 2, 3, 4, or 5.

8. The compound of claim 7, where m is 0, 1, 2, 3, 4, or 5.

9. The compound of claim 7, where n is 0, 1, 2, 3, 4, or 5.

10. A composition comprising one or more compounds represented by one or more of the following formulas:

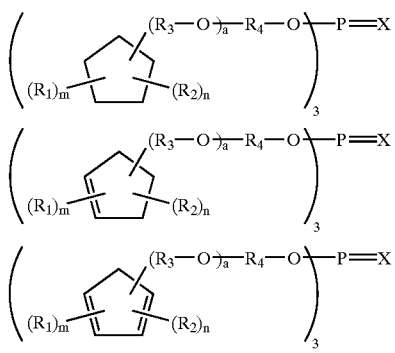

wherein a is 0, 1, 2, 3, 4, 5, 6, 7, 8, 9, or 10; m and n are zero or a positive integer; the sum of m+n is greater than zero; $R_1$, $R_2$, $R_3$, and $R_4$ are individually a hydrocarbyl group; X is either oxygen or sulfur.

11. The composition of claim 10, where the sum of m and n is, 1, 2, 3, 4, or 5.

12. The composition of claim 10, where m is 0, 1, 2, 3, 4, or 5 and the sum of m and n is 1, 2, 3, 4 or 5.

13. The composition of claim 10, where n is 0, 1, 2, 3, 4, or 5 and the sum of m and n is 1, 2, 3, 4 or 5.

14. A composition comprising one or more compounds represented by one or more of the following formulas:

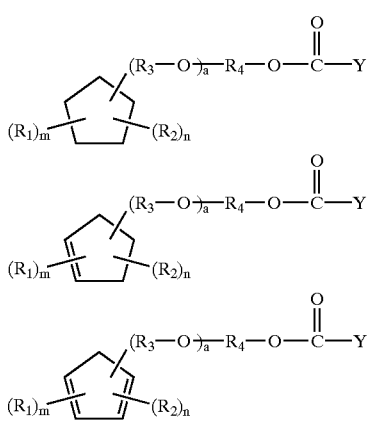

wherein a is 0, 1, 2, 3, 4, 5, 6, 7, 8, 9, or 10; m and n are zero or a positive integer; the sum of m+n is greater than zero; $R_1$, $R_2$, $R_3$, and $R_4$ are individually a hydrocarbyl group; Y is —OH; —NH$_2$,

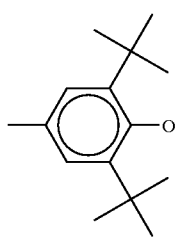

—OH; or —(CF$_2$)$_b$—F, where b is 1, 2, 3, ..., or 20.

15. The composition of claim 14, where the sum of m and n is, 1, 2, 3, 4, or 5.

16. The composition of claim 15, where m is 0, 1, 2, 3, 4, or 5.

17. The composition of claim 14, where n is 0, 1, 2, 3, 4, or 5 and the sum of m and n is 1, 2, 3, 4 or 5.

18. A composition comprising one or more compounds represented by one or more of the following formulas:

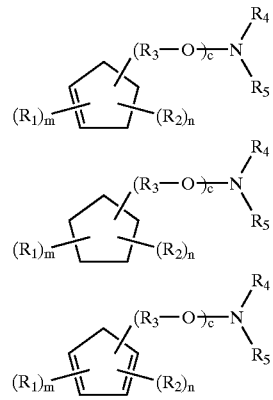

wherein c is 0, 1, 2, 3, 4, 5, 6, 7, 8, 9, or 10; m and n are zero or a positive integer; the sum of m+n is greater than one; $R_1$, $R_2$, and $R_3$ are individually a hydrocarbyl group; $R_4$ and $R_5$ individually are hydrogen or hydrocarbyl.

19. The composition of claim 18, where the sum of m and n is, 2, 3, 4, or 5.

20. The composition of claim 18, where m is 0, 1, 2, 3, 4, or 5 and the sum of m and n is 1, 2, 3, 4 or 5.

21. The composition of claim 18, where n is 0, 1, 2, 3, 4, or 5 and the sum of m and n is 1, 2, 3, 4 or 5.

22. A composition comprising one or more compounds represented by one or more of the following formulas:

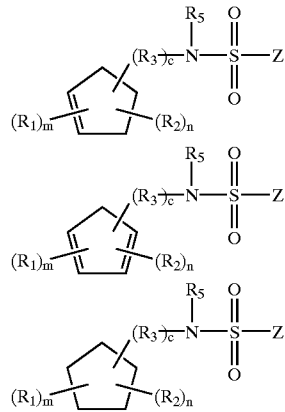

wherein c is 0, 1, 2, 3, 4, 5, 6, 7, 8, 9, or 10; m and n are zero or a positive integer; the sum of m+n is greater than zero; $R_1$, $R_2$, and $R_3$ are individually a hydrocarbyl group; $R_5$ is hydrogen or hydrocarbyl; Z is hydrocarbyl or —(CF$_2$)$_b$—F where b is 1, 2, 3, . . . , or 20.

23. The composition of claim 22, where the sum of m and n is, 1, 2, 3, 4, or 5.

24. The composition of claim 22, where m is 0, 1, 2, 3, 4, or 5 and wherein the sum of m and n is 1, 2, 3, 4, or 5.

25. The composition of claim 22, where n is 0, 1, 2, 3, 4, or 5 and wherein the sum of m and n is 1, 2, 3, 4, or 5.

26. A composition comprising one or more compounds represented by one or more of the following formulas:

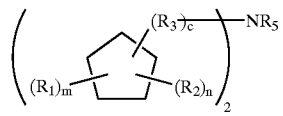

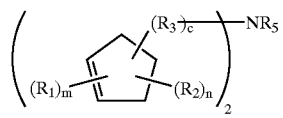

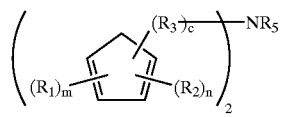

wherein c is 0, 1, 2, 3, 4, 5, 6, 7, 8, 9, or 10; m and n are zero or a positive integer; the sum of m+n is greater than zero; $R_1$, $R_2$, and $R_3$ are individually a hydrocarbyl group; $R_5$ is hydrogen or hydrocarbyl.

27. The composition of claim 26, where the sum of m and n is, 1, 2, 3, 4, or 5.

28. The composition of claim 26, where m is 0, 1, 2, 3, 4, or 5 and wherein the sum of m and n is 1, 2, 3, 4 or 5.

29. The composition of claim 26, where n is 0, 1, 2, 3, 4, or 5 and wherein the sum of m and n is 1, 2, 3, 4 or 5.

30. A composition comprising one or more compounds represented by one or more of the following formulas:

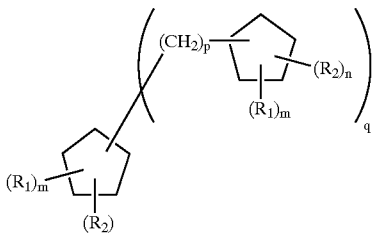

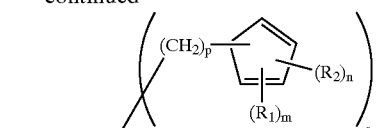

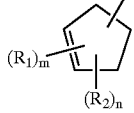

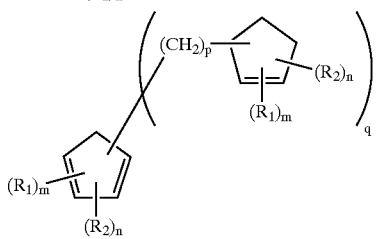

wherein p is 1, 2, 3, . . . , or 10; q is 1, 2, 3, . . . , or 10; m and n are zero or a positive integer; the sum m+n is greater than one; $R_1$ and $R_2$ are individually a hydrocarbyl group.

31. The composition of claim 30, where the sum of m and n is, 2, 3, 4, or 5.

32. The composition of claim 30, where m is 0, 1, 2, 3, 4, or 5 and wherein the sum of m and n is 2, 3, 4 or 5.

33. The composition of claim 30, where n is 0, 1, 2, 3, 4, or 5 and wherein the sum of m and n is 2, 3, 4 or 5.

34. The compound 3-[tris(2-octyldodecyl) cyclopentadienyl]propionitrile.

35. The compound Bis-[tris(2-octyldodecyl)cyclopentyl 3-propyl]amine.

36. The compound 3-[tris(2-octyldodecyl)cyclopentyl] propyl amine.

37. The compound 2-[2-tris(2-octyldodecyl) cyclopentadienyl ethoxy]ethanol.

38. The compound 2-[2-tris(2-octyldodecyl)cyclopentyl]-ethoxy ethanol.

39. The compound 3,5-di-tertiary-butyl 4-hydroxy benzoic ester of [2-tris(2-octyldodecyl)cyclopentyl]-ethoxy ethanol.

40. The compound Di-(n-decal)cyclopentane crosslinked by —$(CH_2)_{10}$— groups.

* * * * *